United States Patent
Shalaby

(10) Patent No.: US 6,703,035 B2
(45) Date of Patent: Mar. 9, 2004

(54) ABSORBABLE ε-CAPROLACTONE COPOLYMERS

(75) Inventor: Shalaby W. Shalaby, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 116 days.

(21) Appl. No.: 10/087,512

(22) Filed: Mar. 1, 2002

(65) Prior Publication Data

US 2002/0114840 A1 Aug. 22, 2002

Related U.S. Application Data

(63) Continuation-in-part of application No. 09/713,860, filed on Nov. 16, 2000, now Pat. No. 6,485,749, which is a division of application No. 09/103,142, filed on Jun. 29, 1998, now Pat. No. 6,197,320, which is a continuation-in-part of application No. 08/660,089, filed on Jun. 3, 1996, now Pat. No. 5,773,563, which is a continuation of application No. 08/212,174, filed on Mar. 11, 1994, now Pat. No. 5,522,842.

(51) Int. Cl.[7] .............................. A01N 25/34; A61K 9/00
(52) U.S. Cl. ........................ 424/408; 424/486; 424/484; 424/93.7; 606/230; 606/231
(58) Field of Search ................................. 424/486, 484, 424/489, 93.7, 408; 606/230, 231

(56) References Cited

U.S. PATENT DOCUMENTS

| | | | |
|---|---|---|---|
| 5,773,563 A | * | 6/1998 | Shalaby ....................... 528/354 |
| 6,197,320 B1 | * | 3/2001 | Shalaby ....................... 424/408 |
| 6,485,749 B1 | * | 11/2002 | Shalaby ....................... 424/486 |

* cited by examiner

Primary Examiner—Alton N. Pryor

(57) ABSTRACT

This invention deals with crystalline, nitrogen copolyester lubricant coating devices comprising sutures, wherein said lubricant comprises a triaxial copolyester chain with a central nitrogenous base or a copolyester with more than one carboxylic group ionically linked to a basic amino acid.

2 Claims, No Drawings

ABSORBABLE ε-CAPROLACTONE COPOLYMERS

This application is a Continuation-in-part of U.S. Ser. No. 09/713,860 now U.S. Pat. No. 6,485,749, entitled "Absorbable ε-Caprolactone Copolymers and Medical Devices", filed Nov. 16, 2000, which is a Divisional of U.S. Ser. No. 09/103,142, entitled "Absorbable ε-Caprolactone Copolymers and Medical Devices", filed Jun. 29, 1998, now U.S. Pat. No. 6,197,320, which is a Continuation-in-part of U.S. Ser. No. 08/660,089, entitled "Absorbable ε-Caprolactone Copolymers", filed Jun. 3, 1996, now U.S. Pat. No. 5,773,563, which is a Continuation of U.S. Ser. No. 08/212,174, entitled "Absorbable ε-Caprolactone Copolymers as Suture Coatings displaying Autocatalyzed Hydrolysis", filed Mar. 11, 1994, now U.S. Pat. No. 5,522,842.

FIELD OF THE INVENTION

BACKGROUND OF THE INVENTION

This invention relates to crystalline, low melting, ε-caprolactone polymers bearing basic amine functionalities which are linked to the ester chain ionically or covalently to induce catalyzed hydrolysis. The ester components can be derived from ε-caprolactone with or without small amounts of glycolide, and/or or similar lactones. Such polymers with accelerated absorption profiles are especially adapted for use as transient coatings for absorbable multifilament surgical sutures (and other medical implants).

Multifilament surgical sutures such as Dexon® polyglycolide multifilament suture typically require a surface coating to improve their handling and knotting characteristics. Capitalizing on the desirable low melting temperature, crystallinity, and rheological properties of polycaprolactone and its copolymers as coating materials, several compositions based on this polymer were investigated as coatings for surgical sutures. Recognizing the fact that the ε-caprolactone homopolymer is essentially non-absorbable led to the development of copolymers of ε-caprolactone with variable amounts of more absorbable monomers to improve the coating absorbability. U.S. Pat. No. 4,624,256 discloses a suture coating copolymer of at least 90 percent ε-caprolactone and a biodegradable monomer and optionally a lubricating agent. Examples of monomers for the biodegradable polymers disclosed include glycolic acid and glycolide, as well as well-known monomers typically used to prepare absorbable polymer fibers or coatings for multifilament sutures. U.S. Pat. Nos. 4,788,979 and 4,791,929 disclose a bioabsorbable coating of a copolymer of at least 50 percent ε-caprolactone and glycolide. Sutures coated with such polymers are reported to be less stiff than sutures coated with other materials and the physical properties of the coated suture are also reported to be acceptable. U.S. Pat. No. 4,994,074 discloses copolymers of a predominant amount of ε-caprolactone, the balance being glycolide and glycolic acid. The use of glycolic acid as a comonomer into the copolymers of this invention was reported to increase the rate of absorption of the copolymer when used as a coating for multifilament surgical sutures.

Unfortunately, the problem of adequate bioabsorbability of ε-caprolactone-based polymers without detrimental effects on their desirable properties as coatings still remains. Specifically, the use of sufficient amounts of glycolide to achieve sufficient absorbability of the copolymeric coating can compromise its crystallinity and melting characteristics, for it may become amorphous or liquid near room temperature. On the other hand, the strategy of using glycolic acid to achieve the reported results in coating absorbability does limit the ability to produce sufficiently long chain molecules to achieve optimum frictional properties, due to glycolic acid's known properties as both a ring-opening initiator chain terminator. Thus, a totally new approach to modifying the absorbability of polycaprolactone and its copolymers without affecting their desirable properties as suture coatings (or coatings for surgical devices) would be a more desirable goal.

SUMMARY OF THE INVENTION

The present invention provides a bioabsorbable, crystalline, nitrogenous copolyester lubricant coating for surgical devices, wherein the lactone derived component of the chain sequences are based on 90 percent to 98 percent ε-caprolactone-based units and 2 percent to 10 percent of glycolide-based units, having improved absorbability, as measured by rate or duration of sustained autocatalytic. In one embodiment of the present invention, improved absobabilility is provided the central location of the nitrogen of a tertiary amine, to which the polymer chains are covalently linked. The central, highly basic amine provides the maximum continued, sustained autocatalytic effect for the hydrolytic degradation of the copolyester chain. This embodiment of the invention is made using triethanolaine (TEA) as an initiator for the ring-opening polymerization of a mixture of cyclic monomers containing more than 85% ε-caprolactone.

In another embodiment of the present invention, improved absorbability is achieved by a copolyester polymer having two or more carboxylic groups per chain to which is ionically or covalently bound a basic amino acid. The increased number of basic amino acid groups per chain produces the improved absorbability. This structure highly absorbable structure is made using di- or tri- hydroxy acids as initiators. Use of these initiators doubles or triples the the carboxylic content of the polymeric chain over chains of comparable molecular weight made using glycolic acid.

The polymer molecular weight is less than 20 kDa. The coating may be advantageously applied to a variety of surgical devices, such as surgical sutures and staples, or facia fasteners as well as other surgical closure devices, and endovascular stents. In addition, the polyesters bearing the amine-functionalities which are the subject of this invention, and coatings derived therefrom, can be used alone or as carriers or matrices for viable cells and vaccines, or as a coating containing bioactive agents such as growth factors, antimicrobials and antibiotics.

DETAILED DESCRIPTION OF THE INVENTION

Polyesters comprising predominantly ε-caprolactone polymer sequences generally refers to polymers with ε-caprolactone-based sequences of greater than 80 mole percent, the monomer compositions from which the polymers of this invention are derived. ε-Caprolactone is the predominant component of the polyester because of its low melting, exceptionally low glass transition temperature ($T_g$) and its ability to enhance the surface physical properties of coated multifilament sutures. Preferably, the amount of ε-caprolactone used in the synthesis of the polyester ranges from 90 to 99, more preferably, 96 to 99 mole percent. For copolyesters, of this invention, the remaining comonomers are preferably glycolide and/or glycolic acid. Other lactones such as lactide and p-dioxanone and/or their corresponding hydroxy acids can be used. The hydroxy acids can be used, specifically as chain initiators to control the polyester molecular weight, as determined in terms of their inherent viscosities (I.V.) as approximately 0.1 dl/g solutions in chloroform, and/or to provide chains with a carboxylic end group. The basic nitrogenous polyesters that are the subject of this invention, are to have I.V. or 0.05 to 0.35 dl/g and, preferably, 0.05 to 0.25 and, more preferably 0.10 to 0.20 dl/g.

The present invention deals with two definite improvements over the prior art disclosed in U.S. Pat. No. 6,197,320. The first improvement deals with use of di- or tri-carboxylic hydroxy acids as initiators for the ring-opening polymerization of a mixture of cyclic monomers containing more than 85% ε-caprolactone. Using di- or tri-carboxylic hydroxy acids as initiators, results in doubling or tripling the carboxylic content of the polymeric chain of comparable molecular weight made under similar conditions using glycolic acid. This, in turn, allows for including higher amounts of the basic amino acid per chain as counter ions of the carboxylate anions and hence, increases the rate of autocatalytic hydrolysis of the copolyester. The second improvement deals with the use of triethanolamine (TEA) as an initiator for the ring-opening polymerization of a mixture of cyclic monomers containing more than 85% ε-caprolactone. Using TEA as an initiator yields a nitrogenous copolyester with (1) symmetrically branched structure; and (2) a central 3° amine group. This, in turn, increases the degree of toughness of the crystalline coating and minimizes its tendency to delaminate, particularly when used as a coating for braided sutures. Having a central, highly basic amine insures the availability of the amine group through most of the life of the copolyester and hence maximizes the continued sustained autocatalytic effect for hydrolytic degradation of the copolyester chain.

The coating can be applied to the braided suture as a low viscosity melt at temperatures between 70° C. and 100° C. and, preferably, 70° C. and 90° C. Excess coating can be removed by passing through a pad of non-woven fabric, e.g., polypropylene or a sizing die. More traditional methods of coating application can entail the use of 1 to 15 percent solution and, preferably, 2 to 10 percent in an organic solvent such as toluene at room temperature or between 25° C. and 50° C. Other solvents or mixture of solvents can be used as substitutes for toluene or acetone. The coated suture can be further treated thermally to insure even distribution of the coating on the braid components. Typical sutures which can be coated with the compositions which are the subject of this invention include those made of polyglycolide and polyethylene terephthalate. Depending on the suture size, the percent add-on of the coating can be varied between 1 and 10 percent and, preferably, 1.5 to 4.5 percent as the suture decreases from about size #1 to about size #6-0. At such level of coating, the suture handling and tie-down characteristics are improved substantially without compromising other properties such as pliability, surface appearance, and knot strength and security.

The coatings which are the subject of this invention can be used to coat synthetic multifilament yarn constructed for use as a dental floss using a similar application protocol to those used for suture coating. For dental floss, a higher coating add-on than those used for suture is preferred in certain constructions and sizes.

The absorption profile of the coating is such that it will not affect that of an absorbable suture to any discernable extent. Typically, when representative coatings subject of this invention are used on polyethylene terephthalate sutures incubated in a phosphate buffer at 37° C. and pH of 7.25 lose 50 to 100 percent of their original mass in two to six months.

The following examples illustrate the claimed invention and are in no way intended to limit its scope.

EXAMPLE 1

Preparation of 95/5 ε-Caprolactone/glycolide Copolymer Initiated with Malic Acid A mixture of ε-caprolactone (136.98 g, 1.2016 mole), glycolide (7.32 g, 0.0631 mole), L-malic acid (16.1 g, 0.12 mole), and stannous octoate (0.632 ml of 0.2 M solution toluene, $1.264 \times 10^{-4}$ mole), was charged into a predried glass reactor equipped for mechanical stirring and providing a dry nitrogen environment. The polymerization mixture was charged and heated at 40° C. under reduced pressure for about 15 minutes and then purged with dry nitrogen. The polymerization was achieved by heating the reactants to 150° C. for 4 hours. The resulting polymer was cooled, isolated, and characterized for identity by NMR and IR, molecular dimension by GPC, and thermal properties by DSC. Key analytical data can be summarized as follows:

$T_m$=46° C. $\Delta H_f$=54 J/g $M_w$(GPC in DCM)=5.95 kDa

EXAMPLE 2

Preparation of 95/5 ε-Caprolactone/glycolide Copolymer Initiated with Malic Acid This copolymer was made to have a higher molecular weight than that of Example 1. Therefore, with the exception of using a smaller amount of malic acid (13.045 g, 0.0974 mole) all other polymerization charge and conditions are similar to those described in Example 1. Key analytical data can be summarized as follows:

$T_m$=45° C. $\Delta H_f$=67 J/g $M_w$(GPC in DCM)=7.10 kDa

EXAMPLE 3

Preparation of 95/5 ε-Caprolactone/glycolide Copolymer Initiated with Malic Acid This copolymer was made to have a higher molecular weight than that of Example 1. Therefore, with the exception of using a much smaller amount of L-malic acid (11.306 g, 0.084 mole), all other polymerization charges and conditions are similar to those described in Example 1. Key analytical data can be summarized as follows:

$T_m$=47° C. $\Delta H_f$=65 J/g $M_w$(GPC in DCM)=7.72 kDa

EXAMPLES 4–6

Preparation of 95/5 ε-Caprolactone/glycolide Copolymers Initiated with Triethanolamine Following polymerization conditions similar to those used in Example 1, three polymers were made using different amounts of triethanolamine as in Examples 3, 4, and 5. The amounts of monomers, triethanolamine and stannous octoate used are summarized in Table I. Analytical data of the resulting copolymers are also provided in Table I.

TABLE I

Examples 4–6
Polymerization Charge and Analytical Data of Resulting Copolymers

|  | Example 4 | Example 5 | Example 6 |
|---|---|---|---|
| Polymerization Charge | | | |
| Caprolactone | ← 142.4 g, 1.249 mole → | | |
| Glycolide | ← 7.6 g, 6.57 × $10^{-2}$ mole → | | |
| Triethanolamine | 6.54 g (4.3 × $10^{-2}$ mole) | 7.8 g (5.2 × $10^{-2}$ mole) | 4.9 g (3.29 × $10^{-2}$ mole) |
| Stannous Octoate as 0.2 M solution in toluene | ← 0.655 ml (1.31 × $10^{-4}$ mole) → | | |
| Analytical Data | | | |
| $M_w$ (GPC), kDa | 10.80 | 9.05 | 14.30 |
| $T_m$, ° C. | 41 | 41 | 48 |
| $\Delta H_f$, J/g | 66 | 56 | 69 |

Many modifications and variations of this invention can be made without departing from its spirit and scope, as will be apparent to those skilled in the art. The specific embodiments described above are offered by way of example only, and the invention is to be limited only by the terms of the appended claims, along with the full scope of equivalents to which such claims are entitled. The various patents and publications mentioned herein are hereby incorporated herein by reference.

What is claimed is:

1. A bioabsorbable, crystalline, nitrogenous copolyester lubricant coating for surgical devices comprising surgical sutures, staples, syringes, and endovascular stents, wherein the polymer molecular weight is less than 20 kDa, and the copolyester chain sequences comprises about 90 percent to 98 percent ϵ-caprolactone units and about 2 percent to 10 percent of glycolide units covalently linked to a central nitrogen of a tertiary amine.

2. A bioabsorbable crystalline, nitrogenous copolyester lubricant coating for surgical devices comprising sutures, staples, syringes, wherein the polymer molecular weight is less than 20 kDa, and its copolyester chain sequences comprise about 90 percent to 98 percent of ϵ-caprolactone units and about 2 percent to 10 percent of glycolide units, and said polymer has two or more carboxylic groups per chain to which is ionically or covalently bound a basic amino acid.

* * * * *